United States Patent [19]

Reuter et al.

[11] 4,011,312

[45] Mar. 8, 1977

[54] PROLONGED RELEASE DRUG FORM FOR THE TREATMENT OF BOVINE MASTITIS

[75] Inventors: Gerald L. Reuter; Andrew G. Tsuk, both of Plattsburgh, N.Y.

[73] Assignee: American Home Products Corporation, New York, N.Y.

[22] Filed: June 25, 1975

[21] Appl. No.: 590,358

[52] U.S. Cl. .................................. 424/78; 424/115; 424/116; 424/227
[51] Int. Cl.$^2$ ................ A61K 31/765; A61K 35/66
[58] Field of Search ............................ 424/227, 78

[56] References Cited
UNITED STATES PATENTS

| | | | |
|---|---|---|---|
| 3,755,558 | 8/1973 | Scribner | 424/78 |
| 3,773,919 | 11/1973 | Boswell et al. | 424/78 |
| 3,887,699 | 6/1975 | Yolles | 424/78 |

*Primary Examiner*—Sam Rosen
*Attorney, Agent, or Firm*—Stephen Venetianer

[57] ABSTRACT

A prolonged release drug dosage form for the treatment of bovine mastitis, specifically suited for dry cow treatment, consists of an antimicrobial agent dispersed in a matrix of a low molecular weight polyester of glycolic and lactic acids, and shaped as a cylindrical bougie for facile insertion into the teat canal. Said polyester erodes by hydrolysis in the bioenvironment, providing a continuous release of the medication throughout the desired duration of the treatment. The low molecular weight polyesters have a glycolic acid content of about 60 to 80 mole percent, a lactic acid content of about 20 to 40 mole percent, and a molecular weight less than 2000.

3 Claims, No Drawings

PROLONGED RELEASE DRUG FORM FOR THE TREATMENT OF BOVINE MASTITIS

BACKGROUND OF THE INVENTION

1. Field of the Invention

Bovine mastitis is a serious problem, common in both lactating dairy-type and beef-type animals. The management of this disease is practiced mostly on the dairy-type animal where daily udder handling and treatment is readily accomplished. Mechanical milking machines may have caused an increased incidence of mastitis; the true origins of the disease remain unknown. Bacterial organisms identified from affected glands are varied; however, the species of streptococcus and staphlococcus are most commonly isolated.

Good animal husbandry practice offers a lower general indidence of mastitis. Antibiotics and chemotherapeutic agents have also demonstrated advantage in restoring affected animals back to healthy milk production. Vaccination has been shown to be useful in minimizing mastitic attack in dairy goats; however, it has not been demonstrated to be useful in cattle.

The control of mastitis in milk-producing animals is, therefore, relegated to good management, selected animals, and medicinal agents. The medications are used both for acute mastitic outbreaks and as prophylactic remedies as dry cow preparations. Of special significance are dosage forms which release the medication in a sustained manner over several days, enabling the complete eradication of the causative organism and guarding against reinfection from the contaminated environment.

A major use for such dosage forms is in dry cow treatments, that is during the approximate 4-week to 10-week period of time immediately preceding the delivery of a calf. The delivery time is also known as the time of freshening, suggesting the new lactation cycle. A treatment approach during the dry period, nonlactating time, reduces the potential of contamination of the milk supply by medicinal agents and provides what should be an effective time exposure of the medication in the udder tissue.

2. Description of Prior Art

Present products available are formulations of medicaments in aqueous, glycol, or vegetable oil-type vehicles. For more prolonged release of medicaments in the udder, mineral oil and vegetable oil with gellants such as amorphous silicon dioxide, aluminum stearates, and emulsifier-type agents are used. The capability for varying the composition of the presently employed ingredients to provide for long term release of medication is limited. The release of the medication relies on its physical liberation from the nonwater soluble and nonerodible vehicle and, thus, is not subject to accurate control in the udder.

A further drawback of present mastitis treatment formulations is that they may harbor pathogenic organisms. Some formulations are sterile to obviate this hazard, others may be pasteurized, and still others may pay no regard to this problem. Enteric pathogenic organisms have been isolated from mineral oil, peanut oil, and other pharmaceutic oils. To minimize problems of this type, preservatives, e.g., chlorobutanol, have been employed.

A further drawback of present formulations, which are based on nonerodible vehicles such as mineral oil, is that these vehicles may persist in the udder or find their way into the milk supply.

DESCRIPTION OF THE INVENTION

It has now been found that an antimicrobial agent incorporated in a bioerodible matrix made from a polyester of glycolic and lactic acid is an effective prolonged release dosage form for the treatment of mastitis, especially for dry cow treatment. The release of the drug is accomplished by the erosion of the matrix which is readily controlled by manipulation of the copolymer composition, the molecular weight of the polymer, and the amount of drug incorporated in the matrix. The low molecular weight polyesters melt at moderate temperatures to moderately viscous fluids, in which the drug is readily dispersible. Surprisingly, the above mentioned polyesters were found to be self-sterilizing and apparently do not support the growth of tested strains of pathogens. Yet, the polyester material was found nonirritating in the cow's udder. The polyesters erode by hydrolysis to glycolic and/or lactic acids, thus leaving no objectionable residues in the udder or milk.

The polyesters useful in the solid dosage forms of the invention are those having a molecular weight below 2000, a glycolic acid content of about 60 to 80 mole percent, and a lactic acid content of about 20 to 40 percent as described in U.S. Pat. No. 2,362,511 issued Nov. 14, 1944 to Teeters, the disclosure of which is incorporated herein by reference.

The antimicrobial content of the solid dosage form can range from about 30 to 70% by weight of the dosage form. The dosage forms are prepared by simply heating the polyester to a temperature of about 60°–80° C., dispersing therein the antimicrobial agent and thereafter rapidly cooling the admixture.

Advantageously the dosage forms are elongated and are prepared, for example, by drawing the molten mix into a polyethylene tube and allowing the mix to cool and solidify. Such a dosage form is in the shape of a bougie having a crayonlike shape about 5 centimeters in length and a diameter less than 0.5 centimeter. The bougie is inserted into the teat canal through the teat sphincter where it releases effective amounts of antimicrobial agent continuously for several weeks.

Antimicrobial agents which can be employed are those effective against species of streptococcus and/or staphlococcus and include broad spectrum antibiotics, such as chlortetracycline, oxytetracycline and tetracycline, and other antibiotics, either singly or in combination, such as: streptomycin, dihydrostreptomycin, the bacitracins, neomycin, polymixin-B, chloramphenicol, erythromycin, amphotericin-B, colistin, ampicillins, the penicillins, the cephalosporins, the cloxacillins, lincomycin, nalidixic acid, novobiocin, kanamycin, ketasomycin, oleandomycin, framycetin, nitrofurazone, furazolidone, furaltadone, sulfonamides, complexed halogens, and other drugs specifically useful in the treatment of bovine mastitis and generally useful in topical medicinal applications.

DETAILED DESCRIPTION OF THE INVENTION

The preparation of the polyesters useful in this invention is described in the following examples.

EXAMPLE I

Pure crystalline glycolic acid, 351 grams, USP lactic acid (85%), 131 milliliters, and 774 milliliters of distilled water were introduced into a 1 liter resin kettle equipped with a nitrogen inlet bubbling tube, thermometer, heating mantle, condenser and receiver. Under a slow stream of nitrogen, water was distilled off under atmospheric pressure until the pot temperature reached about 180° C and the distillation was then continued under aspirator vacuum with nitrogen bubbling through at a reduced rate to provide stirring and to avoid bumping until the pot temperature reached 219° C, a total distillation time of about 12 hours. The resin kettle was opened and its hot contents were poured into a beaker, where it soon solidified. It is soluble in most commmon solvents.

Determination of molecular weight: an amount of the product was dissolved in hot dimethylsulfoxide, and the free carboxyl groups were assayed by non-aqueous acidimetry. The acid number obtained was 0.543 miliequivalents carboxyl per gram of product, corresponding to a number average molecular weight of about 1800.

This lactic acid modified polyglycolide containing 75 mole % glycolic acid, with a molecular wight of 1800, was used to make the dosage forms of this invention by mixing one part by weight of crystalline chlortetracycline hydrochloride with two parts by weight of the molten polyester in a Brabender Mixer then drawing the fluid mix into a polyethylene tube by vacuum and allowing the mix to cool and solidify. The polyethylene tube can be refrigerated and cut into bougie size lengths of about 5 centimeters and the elongated dosage form withdrawn and used as desired.

Dissolution tests in vitro have shown that the drug is released from the matrix continuously at adequate rates. Also, tests in cows' udders have demonstrated that the polyester material in bougie form offers no indications of udder irritation. Irritation was adjudged by somatic cell counting and the California Mastitis Test methods. Both of these techniques are known to people versed in dairy management. The somatic cell count technique is described by Schonberg in Milchkunde And Milchhygiene (1956) and the California Mastitis Test is described in Journal of American Veterinary Medical Association, Volume 130, pages 199–204 by Shlam and Noorlander. A bougie 5 centimeters long and 0.5 centimeter in diameter of this example was found to provide effective medication for four to six weeks, almost the extent of the entire dry period.

In general, the literature has numerous references to show that glycolic/lactic copolyesters and their hydrolysis products are nontoxic and harmless when exposed to human or animal tissues.

EXAMPLE II

Pure crystalline glycolic acid, 217 grams, USP lactic acid (85%), 105 milliliters, and 394 milliliters of distilled water were introduced into the resin kettle as in Example 1, and water was distilled off under atmospheric pressure until the pot temperature reached about 180° C and the distillation was then continued under aspirator vacuum until the pot temperature reached 205° C, a total distillation time of about 10 hours. The acid number of the cooled solid melt was 0.819 milliequivalents carboxyl per gram of product, indicating a molecular weight of 1200.

One part by weight of this polyester containing 70 mole % glycolic acid, with a molecular weight of 1200, and one part by weight of oxytetracycline hydrochloride are intimately mixed in a Bradender Mixer. The admixture is then injected into molds to provide elongated dosage forms with tapered ends as bougees.

EXAMPLE III

Glycolic acid in aqueous solution, 570 milliliters containing 465 grams of acid, USP lactic acid (85%), 140 milliliters, and 470 milliliters of distilled water were introduced into the resin kettle as in Example 1, and water was distilled off under atmospheric pressure until the pot temperature reached about 180° C and the distillation was then continued under aspirator conditions until the pot temperature reached 255° C, a total distillation time of about 16 hours. The acid number of the cooled solid melt was 0.670 milliequivalents carboxyl per gram of product, indicating a molecular weight of 1500.

Two parts by weight of this polyester containing 79 mole % glycolic acic, with a molecular weight of 1500, and one part by weight of tetracycline hydrochloride are intimately mixed in a Brabender Mixer. The mixture is then injected into molds to provide elongated dosage forms with tapered ends as bougies.

EXAMPLE IV

Glycollic acid in aqueous solution, 314 milliliters containing 794. milligrams per milliliter by titration, USP lactic acid (85%), 190 milliliters, and 300 milliliters of distilled water were introduced into the resin kettle as in Example 1 and water was distilled off under atmospheric pressure until the pot temperature reached about 180° C and the distillation was then continued under aspirator conditions until the pot temperature reached 201° C, a total of about 16 hours. The acid number of the cooled solid melt was 0.81 milliequivalents carboxyl per gram of product, indicating a molecular weight of 1200.

One part by weight of this lactic acid modified polyglycolide containing 63 mole % of glycolic acid and one part by weight of an admixture of neomycin and polymixin B containing 80 weight percent neomycin is admixed and formed into bougies as described in the previous examples.

EXAMPLE V

In this example, a portion of the polyester-chlortetracycline mix of Example I was ground and the resulting small particles or beads were suspended in peanut oil to provide a suspension containing about 50% by weight of solids. The suspension was found to be self-sterilizing. It can be packaged in disposable syringes and when infused into cow's udders, was found to be effective medicinally with no indication of udder irritation.

As the glycolic acid content increases, the resulting polyesters become harder, their softening point increases, and they show less tendency toward caking, all of these being desirable changes. Polyesters with a glycolic acid content between about 60 and 80 mole % are transparent brittle solids melting at or below 60° C.

In addition to the polyester and antimicrobial agent, other pharmaceutic aids can be incorporated into the dosage forms of this invention in relatively minor amount, i.e. up to about 5% by weight of the dosage form. These pharmaceutic aids include cobalt chloride, certain steroids, enzymes, chlorbutanol, polyvinylpyrrolidone, benzyl alcohol, amorphous silicas, sodium chloride, fatty acids and emulsifiers.

In addition to the peanut oil of Example V, other vegetable oils such as castor oil, cottonseed oil, sunflower seed oil, rapeseed oil and corn oil can be employed. Also, glycols such as the polyethylene and polypropylene glycols are suitable. The oil suspensions can contain from about 30 to 50 weight percent of the solid dosage forms of this invention. The suspensions can be packaged in disposable syringes or can by administered by an infusion cannula.

We claim:

1. A bioerodable solid dosage form for the treatment of mastitis comprising from about 30 to 70% by weight of a dosage form of at least one antimicrobial agent intimately dispersed in a polyester of glycolic and lactic acid, prepared by heating the polyester to a temperature of about 60°–80° C, dispersing therein the antimicrobial agent and thereafter rapidly cooling the admixture, the polyester having a molecular weight less than 2,000, a glycolic acid content of about 60 to 80 mole percent, and a lactic acid content of about 20 to 40 mole percent.

2. The dosage form of claim 1 wherein the antimicrobial agent is chlortetracycline.

3. A dosage form for the treatment of mastitis comprising a suspension in a vegetable oil of about 30 to 50% by weight of the subdivided dosage form of claim 1.

* * * * *